United States Patent
Patel et al.

(10) Patent No.: US 10,016,447 B2
(45) Date of Patent: Jul. 10, 2018

(54) PHARMACEUTICAL COMPOSITION HAVING IMPROVED CONTENT UNIFORMITY

(71) Applicant: Intas Pharmaceuticals Ltd, Ahmedabad, Gujarat (IN)

(72) Inventors: Priyank Patel, Ahmedabad (IN); Mayur Patel, Ahmedabad (IN); Mahendra Patel, Ahmedabad (IN); Balvir Singh, Ahmedabad (IN); Ashish Sehgal, Ahmedabad (IN)

(73) Assignee: Intas Pharmaceuticals Ltd., Ahmedabad (IN)

( * ) Notice: Subject to any disclaimer, the term of this patent is extended or adjusted under 35 U.S.C. 154(b) by 0 days.

(21) Appl. No.: 15/512,946

(22) PCT Filed: Sep. 25, 2015

(86) PCT No.: PCT/IB2015/057384
§ 371 (c)(1),
(2) Date: Mar. 21, 2017

(87) PCT Pub. No.: WO2016/046797
PCT Pub. Date: Mar. 31, 2016

(65) Prior Publication Data
US 2017/0304328 A1    Oct. 26, 2017

(30) Foreign Application Priority Data

Sep. 26, 2014 (IN) .......................... 3087/MUM/2014

(51) Int. Cl.
| | | |
|---|---|---|
| *A61K 31/70* | (2006.01) |
| *A61K 31/675* | (2006.01) |
| *A61K 31/685* | (2006.01) |
| *A61K 31/7068* | (2006.01) |
| *A61K 9/20* | (2006.01) |
| *A61K 9/24* | (2006.01) |
| *C07F 9/6584* | (2006.01) |

(52) U.S. Cl.
CPC ............ *A61K 31/675* (2013.01); *A61K 9/209* (2013.01); *A61K 9/2054* (2013.01); *A61K 31/7068* (2013.01); *C07F 9/65846* (2013.01)

(58) Field of Classification Search
CPC .............................. A61K 31/70; A61K 31/675
USPC ..................................... 514/49, 90
See application file for complete search history.

(56) References Cited

U.S. PATENT DOCUMENTS

| | | |
|---|---|---|
| 3,018,302 A | 1/1962 | Bielefeld |
| 5,047,246 A | 9/1991 | Gallian et al. |
| 2001/0046504 A1 | 11/2001 | Engel et al. |

FOREIGN PATENT DOCUMENTS

| | | |
|---|---|---|
| WO | 2010/134025 | 11/2010 |
| WO | 2013/028186 | 2/2013 |
| WO | 2015/044961 | 4/2015 |

OTHER PUBLICATIONS

Shien, et al., "Clinical Efficacy of Capecitabine and Cyclophosphamide (XC) in Patients with Metastatic Breast Cancer", Acta Med. Okayama, vol. 65, No. 4, 2011, pp. 231-237.
Ohno, et al., "Dosage of Capecitabine and Cyclophosphamide Combination Therapy in Patents with Metastatic Beast Cancer", Anticancer Research, vol. 27, 2007, pp. 1009-1014.

*Primary Examiner* — Raymond J Henley, III
(74) *Attorney, Agent, or Firm* — Hamre, Schumann, Mueller & Larson, P.C.

(57) ABSTRACT

This present invention relates to pharmaceutical compositions comprising cyclophosphamide alone and/or in combination with one or more pharmaceutical active ingredients and one or more pharmaceutically acceptable excipients wherein the cyclophosphamide has D90 particle size less than 100 microns.

10 Claims, No Drawings

PHARMACEUTICAL COMPOSITION HAVING IMPROVED CONTENT UNIFORMITY

RELATED APPLICATIONS

This application is related to Indian Provisional Application 3087/MUM/2014 filed Sep. 26, 2014 and is incorporated herein its entirely

FIELD OF THE INVENTION

This present invention relates to pharmaceutical compositions comprising cyclophosphamide alone and/or in combination with one or more pharmaceutical active ingredients and one or more pharmaceutically acceptable excipients wherein the cyclophosphamide has D90 particle size less than 100 microns.

BACKGROUND OF THE INVENTION

The chemical name of cyclophosphamide is 2-[bis(2-chloroethyl)amino]tetrahydro-2H-1,3,2-oxazaphosphorine 2-oxide monohydrate. The compound along with related novel cyclic phosphoric acid ester amides was disclosed and claimed in U.S. Pat. No. 3,018,302. Cyclophosphamide, an anti neoplastic agent classified as an alkylating agent.

Cyclophosphamide is a prodrug, converted in the liver to active forms that have slow down the growth of cancer cells and requires enzymatic and chemical activation to produces active form. Cyclophosphamide is used alone or in combination with other drugs to treat various cancers like metastatic breast cancer, ovarian cancer, and leukemia. When given by orally, cyclophosphamide shows superior efficacy than when it is given intravenously.

U.S. Pat. No. 5,047,246 discloses directly compressible pharmaceutical composition comprising cyclophosphamide and a partially or fully pregelatinized starch. The pharmaceutical composition, when directly compressed into a tablet, exhibits unexpected stability when compared to cyclophosphamide in combination with other direct compression vehicles.

U.S. Patent publication no 20010046504 discloses film-coated tablets with cyclophosphamide as active compound, which in the core comprise cyclophosphamide, one or more fillers, one or more dry binders (but no preswollen starch), flow regulators and lubricants.

The above prior-art discloses that direct compression is desirable method for cyclophosphamide tablet. Further, the U.S. Pat. No. 5,047,246 discloses that wet granulation method has certain drawback, from which one of the problem is dissolution rate of the tablet varies from batch to batch, with some batches having unacceptably low rates.

This problem may arise due to a combination of factors such as non-ideal granule characteristics such as particle size of active pharmaceutical ingredients, particle size differences with excipients, and segregation during manufacturing operations. Further ensuring content uniformity is a pretty significant parameter for efficiency of the treatment. In other terms, dose of an active agent which is required to be contained in a capsule or a tablet in order to provide therapeutic effect is closely related to flow characteristics of the formulation comprising said active agent.

Content uniformity of mixture is said to be achieved when the proportion and particle size of the ingredients is identical all over the mixture. Particle size of active ingredient also plays an important role in achieving content uniformity.

Several products of pharmaceuticals are a blend of various powders or bulk solids. Hence mixing of powders is a very important part of pharmaceutical product development. Further for pharmaceutical formulations there are currently three basics methods used for the product development to increase dissolution rate, flowability, density of API, better distribution of API for low dose formulations. They are the wet granulation method, the dry granulation method and the direct compression method Therefore there is great interest in the industry to understand the interplay of various granule characteristics such as particle size of active pharmaceutical ingredients, particle size distribution and granule loading with tablet content uniformity. Unfortunately, cyclophosphamide is one of the few known compounds which possess the above problems.

However, there is still an existing and continual need to overcome the above mentioned problems. The inventors of the present invention address the need of sufficient flow characteristics and content uniformity by provide a pharmaceutical composition of cyclophosphamide alone and/or in combination with other pharmaceutical active ingredients wherein the cyclophosphamide particles has D90 particle size less than 100 microns.

OBJECTS OF THE INVENTION

The object of the present invention is to provide a pharmaceutical composition comprising cyclophosphamide and one or more pharmaceutically acceptable excipients wherein the cyclophosphamide has D90 particle size less than 100 microns.

Another object of the present invention is to provide a pharmaceutical composition comprising cyclophosphamide alone and/or in combination with one or more pharmaceutical active ingredients and one or more pharmaceutically acceptable excipients, wherein the cyclophosphamide has D90 particle size less than 100 microns.

Another object of the present invention is to provide a pharmaceutical composition comprising a fixed dose combination of cyclophosphamide and capecitabine with one or more pharmaceutically acceptable excipients, wherein the cyclophosphamide has D90 particle size less than 100 microns.

Another object of the present invention is to provide a pharmaceutical composition comprising a fixed dose combination of cyclophosphamide and capecitabine with one or more pharmaceutically acceptable excipients in the form of bilayer tablet, wherein the cyclophosphamide has D90 particle size less than 100 microns.

Another object of the present invention is to provide a pharmaceutical composition comprising a first layer & second layer, wherein the first layer comprises capecitabine and one or more excipients, and the second layer comprises cyclophosphamide and one or more excipients, wherein the cyclophosphamide has D90 particle size less than 100 microns.

Another object of the present invention is to provide a pharmaceutical composition comprising a first layer & second layer, wherein the first layer comprises capecitabine in the amount of 10 to 1500 mg and one or more excipients, and the second layer comprises cyclophosphamide in the amount of 20 to 80 mg and one or more excipients, wherein the cyclophosphamide has D90 particle size less than 100 microns.

Another object of the present invention to provide a bilayer tablet comprising capecitabine in a first layer and cyclophosphamide in a second layer and optionally a film coating that covers both layer, wherein the cyclophosphamide has D90 particle size less than 100 microns.

Another object of the present invention is to provide a process for the preparation of pharmaceutical composition comprising cyclophosphamide and one or more pharmaceutically acceptable excipients, wherein the cyclophosphamide has D90 particle size less than 100 microns.

Another object of the invention is to provide process for the preparation of pharmaceutical composition comprising a first layer & second layer, wherein the first layer comprises capecitabine and one or more excipients, and the second layer comprises cyclophosphamide and one or more excipients, wherein the cyclophosphamide has D90 particle size less than 100 microns.

Another object of the invention is to provide a pharmaceutical composition comprising cyclophosphamide alone and/or in combination with one or more pharmaceutical active ingredients and one or more pharmaceutically acceptable excipients, having content uniformity between 95% and 105%.

In yet another object of the invention is to provide a pharmaceutical composition comprising cyclophosphamide alone and/or in combination with one or more pharmaceutical active ingredients and one or more pharmaceutically acceptable excipients, having acceptance value less than 9 as per USP <905> uniformity of dosage units.

SUMMARY OF THE INVENTION

This present invention relates to pharmaceutical compositions comprising cyclophosphamide alone and/or in combination with one or more pharmaceutical active ingredients and one or more pharmaceutically acceptable excipients wherein the cyclophosphamide has D90 particle size less than 100 microns. The invention is particularly suitable for oral administration and addresses the problem associated with the content uniformity of cyclophosphamide. Further the present invention is an effective, convenient and well-tolerated regimen for Metastatic Breast Cancer.

DETAILED DESCRIPTION

Unless otherwise indicated, terms in this specification are intended to have their ordinary meaning in the relevant art.

An embodiment of the present invention is to provide a pharmaceutical composition comprising cyclophosphamide and one or more pharmaceutically acceptable excipients, wherein the cyclophosphamide has D90 particle size less than 100 microns.

The term "pharmaceutically acceptable" means carriers, excipients, and other formulation ingredients that are compatible with all other pharmaceutical ingredients of a composition and are not deleterious to an individual treated with composition.

The term "content uniformity" means the homogeneity of the cyclophosphamide content among dosage forms after formulation. Content uniformity and acceptance value test can be performed according to revised US Pharmacopoeia chapter <905> Uniformity of dosage units. The term of "Uniformity of dosage unit" is defined as the degree of uniformity in the amount of drug substance among dosage units. According to US pharmacopoeia criteria, the requirements for dosage uniformity is met if the acceptance value of the first 10 dosage unit is less than or equal to 15%.

According to present invention the term "D90 particle size" means that at least 90% of the particles have the stated diameter or less (measured by volume). For example; particles stated to have D90=100 microns means that 90% of the particles have a diameter of 100 microns or less. In a preferred embodiment, the D90 particle size of cyclophosphamide has less than 100 microns.

According to one embodiment of the present invention, the pharmaceutical composition is present in the form of solid dosage form. The solid dosage form can be monolayer tablet, bilayer tablet, multilayer tablet, film-coated tablet, powders, lozenges, sachets and hard gelatin capsules.

According to one of the embodiments, cyclophosphamide present in amount of 10-100 mg, preferably 20-80 mg, more preferably 20-60 mg.

Another embodiment for the present invention is to provide a pharmaceutical composition comprising cyclophosphamide alone and/or in combination with one or more pharmaceutical active ingredients and one or more pharmaceutically acceptable excipients, wherein the cyclophosphamide has D90 particle size less than 100 microns.

In one embodiment of the present invention, the pharmaceutical composition of the present invention further comprises one or more pharmaceutical active ingredients.

In a further preferred embodiment, the pharmaceutical composition of the present invention further comprises capecitabine.

Capecitabine is the most commonly-used agent and has been approved by the Food and Drug Administration in the treatment of Metastatic breast cancer patients resistant to anthracyclines and/or taxanes. Capecitabine widely used in different combination regimen due to better therapeutic & safety profile with lower side effects. In addition, the combination partner of capecitabine play important role for the activation of thymidine phosphorylase (TP) enzyme, which convert the capecitabine to active 5-FU.

With increasing experience of capecitabine after its introduction, many clinicians found that oral administration of cyclophosphamide and capecitabine may have a greater potential for treatment of Metastatic breast cancer due to anti-angiogenesis resulting from the metronomic dosage and upregulation of thymidine phosphorylase by capecitabine. In addition several clinical studies show that the efficacy of cyclophosphamide in combination with capecitabine was more than just additive to synergistic effects.

Another object of the present invention is to provide a pharmaceutical composition comprising a fixed dose combination of cyclophosphamide and capecitabine with one or more pharmaceutically acceptable excipients, wherein the cyclophosphamide has D90 particle size less than 100 microns.

In one embodiment, pharmaceutical composition comprising a fixed dose combination of cyclophosphamide and capecitabine present in solid dosage form, particularly for oral administration. The solid dosage form of fixed dose combination can be monolayer tablet, bilayer tablet, multilayer tablet, film-coated tablet, powders, lozenges, sachets and hard gelatin capsules, more preferably bilayer tablet.

In one of the embodiments of the present invention, is to provide a pharmaceutical composition comprising a first layer & second layer, wherein the first layer comprises capecitabine and one or more excipients, and the second layer comprises cyclophosphamide and one or more excipients, wherein the cyclophosphamide has D90 particle size less than 100 microns.

In one of the embodiments, the pharmaceutical composition according to present invention comprising bilayer tablet comprising a first layer & second layer, wherein the first layer comprises capecitabine and one or more excipients, and the second layer comprises cyclophosphamide and one or more excipients.

In preferred embodiment, a bilayer tablet according to present invention generally contains 50-1800 mg, preferably 100-1500 mg, more preferably 300-800 mg capecitabine; and 10-100 mg, preferably 20-80 mg, more preferably 20-60 mg cyclophosphamide. Presently preferred forms are bilayer tablet comprising 300/20 mg, 400/20 mg, 600/40 mg and 700/30 mg of capecitabine and cyclophosphamide respectively.

In another embodiment, the pharmaceutical composition comprises cyclophosphamide and one or more pharmaceutically acceptable excipients. Pharmaceutically acceptable excipient(s) include but are not limited one or more diluents or fillers, one or more binders, one or more glidants, one or more disintegrants, one or more lubricants, and the like. The amount of each excipient in a solid dosage formulation may vary within ranges conventional in the art. One excipient can perform more than one function.

The fillers or diluents can be selected from the group consisting of but not limited to dibasic calcium phosphate anhydrous, microcrystalline cellulose, lactose, mannitol, sucrose or other sugar or sugar derivatives, low substituted HPC, pregelatinized starch, and combination thereof.

The binder can be selected from the group consisting of but not limited to pregelatinized starch, polyvinylpyrrolidone, povidone, copovidone, hydroxypropylmethyl cellulose, hydroxypropyl cellulose, maize starch, microcrystalline cellulose, and combinations thereof.

The disintegrant can be selected from the group consisting of but not limited to croscarmelose sodium, crospovidone, sodium starch glycolate, starch, pregelatinized starch and combination thereof.

The glidant can be selected from the group consisting of but not limited to colloidal silicon dioxide, talc, stearic acid, palmitic acid, polyethylene glycol, carnauba wax and/or mixtures thereof.

The lubricants can be selected from the group consisting of but not limited to magnesium stearate, calcium stearate, aluminum or calcium silicate, stearic acid, talc and combinations thereof.

The pharmaceutical composition described herein may be prepared by conventional technology well known to those skilled in the art such as wet granulation, dry granulation and direct compression and the like.

In a preferred embodiment the process for the preparation of pharmaceutical composition comprising cyclophosphamide and one or more pharmaceutically acceptable excipients comprising following steps:
(a) co sifting one or more pharmaceutical excipients and preparing a mixture,
(b) granulating the above mixture by using granulation liquid.
(c) dry the above granulate and milling the dried granules
(d) preparing the drug mixture separately by co sifting the cyclophosphamide and one or more pharmaceutically acceptable excipients,
(e) blend the granules obtained in step (c) and drug mixture,
(f) lubricating the above blended drug mixture and compressing in tablets or filled in hard gelatin capsule.

In a further preferred embodiment, drug mixture comprising cyclophosphamide has D90 particle size less than 100 microns.

In a further preferred embodiment, granules containing one or more pharmaceutically acceptable excipients can be prepared by high sheer mixer granulate.

Alternatively the pharmaceutically composition of the present invention can be prepared by direct compression and comprising following steps:
(a) mixing the cyclophosphamide with one or more filler, one or more binder, one or more disintegrant in a suitable mixer
(b) adding one or more lubricant in mixture obtained in step (a) and blending them until obtaining a homogenous powder mixture; and
(c) compressing the final powder mixture into tablets and filled into hard gelatin capsule.

The present invention further provides a process for the preparation of pharmaceutical composition comprising a first layer & second layer, wherein the first layer comprises capecitabine and one or more excipients, and the second layer comprises cyclophosphamide and one or more excipients described herein above, wherein the cyclophosphamide has D90 particle size less than 100 microns.

More preferably in the present invention, the first layer comprising capecitabine can be prepared by any method known in art such as wet granulation, dry granulation and direct compression, more preferably wet granulation.

In the wet granulation process the granulating liquid is a solvent such as purified water, ethanol, isopropanol, acetone or mixture thereof, preferably purified water. The solvent is a volatile component, which does not remain in the final product.

According to present invention a bilayer tablet comprising first layer is prepared by wet granulation comprising following steps:
(a) sifting of capecitabine, one or more filler, one or more disintegrant through appropriate mesh and mixing in a suitable mixer,
(b) dissolving a binder in a solvent to produce a granulation liquid,
(c) carrying out fluid bed granulation using the granulating liquid of step (b) for spraying onto the mixture of step (a),
(d) after completion of the granulation drying and optionally, screening the granulate obtained in step (c),
(e) optionally blending the granulate obtained in step (d) with additional excipients; and,
(f) lubricating the blended granules obtained in step (e) to prepare the final composition of first layer.

Alternatively, binder can be added with the blend obtained in step (a) & further granulation is done with suitable solvent which would act as a granulation liquid.

One more preferred embodiment of the invention the second layer comprising cyclophosphamide can be prepared by conventional technology well known to those skilled in the art such as wet granulation, dry granulation and direct compression and the like as described herein above in details. Further the second layer also comprises one or more pharmaceutically acceptable excipients described herein above.

Further the bilayer tablet optionally comprising film coating that covers both the layers. Film coating material is a polymeric film coating material comprises hydroxypropyl methylcellulose, polyethylene glycol, polysorbate, sodium carboxy methyl cellulose, Talc, Titanium dioxide, simethicon, Eudragit, purified water or colorant.

In one of embodiment, the present invention provide a pharmaceutical composition comprising cyclophosphamide alone and/or in combination with one or more pharmaceutical active ingredients and one or more pharmaceutically acceptable excipients, having content uniformity between 95% and 105%.

In yet another embodiment of the invention is to provide a pharmaceutical composition comprising cyclophosphamide alone and/or in combination with one or more pharmaceutical active ingredients and one or more pharmaceutically acceptable excipients, having acceptance value less than 9 as per USP <905> uniformity of dosage units.

In a preferred embodiment, the present invention provides a pharmaceutical composition comprising cyclophosphamide having content uniformity between 95% and 105%.

In another preferred embodiment, the present invention provides a pharmaceutical composition comprising cyclophosphamide and one or more pharmaceutically acceptable excipients having USP acceptance value having less than 15, preferably less than 10, more preferably less than 9.

In preferred embodiments, the present invention provide a bilayer tablet comprising capecitabine and cyclophosphamide having content uniformity between 95% and 105% wherein the cyclophosphamide D90 particle size has less than 100 microns In another preferred embodiment, the present invention provide a bilayer tablet comprising capecitabine and cyclophosphamide having USP acceptance value less than 15, preferably less than 10, more preferably less than 9, wherein the cyclophosphamide D90 particle size has less than 100 microns.

Content uniformity and acceptance value test can be performed according to revised US Pharmacopoeia chapter <905> Uniformity of dosage units as described herein above.

Further the present invention provides a pharmaceutical composition comprising fixed dose combination of capecitabine and cyclophosphamide thereof have a greater potential for treatment of metastatic breast cancer.

In addition, the present invention provides a better therapeutic efficacy by combined administered of capecitabine and cyclophosphamide rather than when used separately.

EXAMPLES

The present invention has been described by way of example only. It is to be recognized that modifications falling within the scope and spirit of the claims, which would be obvious to a person skilled in the art based upon the disclosure herein, are also considered to be included within the scope of this invention. The scope of the invention is in no manner limited by the disclosed example.

Example 1A

| Ingredients | Qty/Tab (mg) |
|---|---|
| Microcrystalline cellulose | 62.55 |
| Dibasic calcium phosphate, dihydrate | 38.40 |
| Pregelatinized starch | 21.00 |
| Povidone k-90 | 3.40 |
| Purified water | q.s. |
| Cyclophosphamide (D90 = 300 microns) | 21.40* |
| Pregelatinized starch | 4.60 |
| Croscarmelose sodium | 10.00 |
| Talc | 3.40 |
| Colloidal anhydrous silica | 1.700 |
| Magnesium stearate | 3.400 |
| Ferric oxide yellow | 0.150 |
| Total weight | 170.00 |

*Cyclophosphamide 21.5 mg is equivalent to anhydrous Cyclophosphamide 20 mg

Manufacturing Process:
1. Co sift microcrystalline cellulose, dibasic calcium phosphate, dihydrate (milled), Pregelatinized starch and Povidone K-90.
2. Dry mix and granulate the blend of step 1 using Purified water. Dry the granules at 60° C.
3. Separately co-sift cyclophosphamide, pregelatinized starch and croscarmellose sodium.
4. Co sift talc, colloidal anhydrous silica-E and Ferric oxide yellow.
5. Blend the granules of step 2, 3 and 4 in blender for 10 minutes.
6. lubricated the blend obtained in step 5 with magnesium stearate and compressed into tablets.

Example 1B

| Ingredients | Qty/Tab (mg) |
|---|---|
| Microcrystalline cellulose | 62.55 |
| Dibasic calcium phosphate, dihydrate | 38.40 |
| Pregelatinized starch | 21.00 |
| Povidone k-90 | 3.40 |
| Purified water | q.s. |
| Cyclophosphamide (D90 < 100 microns) | 21.40* |
| Pregelatinized starch | 4.60 |
| Croscarmelose sodium | 10.00 |
| Talc | 3.40 |
| Colloidal anhydrous silica | 1.700 |
| Magnesium stearate | 3.400 |
| Ferric oxide yellow | 0.150 |
| Total weight | 170.00 |

*Cyclophosphamide 21.4 mg is equivalent to anhydrous Cyclophosphamide 20 mg

Manufacturing Process

The tablet composition of example 1B was prepared same as the process of example 1A.

Content Uniformity of Example 1A and 1B

Content uniformity of cyclophosphamide tablets was evaluated for 10 individual tablets prepared by example 1A and 1B as per revised US Pharmacopoeia chapter <905> Uniformity of dosage units.

Results:

| | Cyclophosphamide | |
|---|---|---|
| | Example 1A D90 = 300 micron | Example 1B D90 < 100 microns |
| Content uniformity | 103.3%-115.7% | 93%-104.5% |
| Acceptance value | 15 | 8.3 |

Example 1B (pharmaceutical composition comprising cyclophosphamide having D90 particle size less than 100 microns) shows better content uniformity and acceptance value than Example 1A (the composition comprising bigger particle size).

Example 2A

| Ingredients | Qty/Tab (mg) |
|---|---|
| Capecitabine | 400.0 |
| Microcrystalline Cellulose* | 33.27 |
| Lactose anhydrous | 38.43 |
| Croscarmellose Sodium | 13.25 |
| HPMC E-5 | 18.55 |
| Purified Water | q.s. |
| Croscarmellose Sodium | 13.25 |
| Colloidal silicon dioxide | 2.65 |
| Magnesium Stearate | 10.60 |
| Total of Layer I | 530.00 |
| Microcrystalline cellulose | 62.550 |
| Dibasic calcium phosphate, dihydrate (milled) | 38.400 |
| Pregelatinized starch | 21.000 |
| Povidone K-90 | 3.40 |
| Purified water | q.s. |
| Cyclophosphamide (D90 = 300 microns) | 21.40* |
| Pregelatinized starch | 4.60 |
| Croscarmellose Sodium | 10.00 |
| Talc | 3.40 |
| Colloidal anhydrous silica-E | 1.70 |
| Magnesium Stearate | 3.40 |
| Ferric oxide yellow | 0.150 |
| Total Layer II | 170.0 |
| Total Core Tablet weight | 700.00 |
| Polyethylene glycol 4000 | 2.39 |
| Polysorbate 80 | 0.49 |
| Sodiumcarboxymethyl cellulose | 0.39 |
| Talc | 4.74 |
| Titanium Dioxide | 4.74 |
| Eudragit NE30D | 2.152 |
| Ferric oxide yellow | 0.09 |
| Ferric oxide Red | 0.004 |
| Purified water | q.s. |
| Total coated tablet weight | 715.00 |

*Cyclophosphamide 21.4 mg is equivalent to anhydrous Cyclophosphamide 20 mg

Brief Manufacturing Process of Example 2A

Preparation of Capecitabine Layer:
1. Sift capecitabine, microcrystalline cellulose, lactose anhydrous and croscarmellose sodium
2. Place materials of step 1 in fluid bed energizer and dry mix for 5 min at 50° C.
3. Dissolve hypromellose E5 in Purified Water using stirrer.
4. Granulate materials in fluid bed energizer using binder solution of step 3.
5. Dry the granules in fluid bed energizer at 55° C.
6. Sift croscarmellose sodium through and colloidal silicon dioxide and mix with granules of step 5.
7. lubricated the above blend obtained in step 6 with magnesium stearate to prepare the final composition of first layer.

Preparation of Cyclophosphamide Layer:
8. co sift microcrystalline cellulose, dibasic calcium phosphate, dihydrate (milled), Pregelatinized starch and Povidone K-90.
9. granulate the above mixture obtained in step 9 using Purified water.
10. Dry and mill the above granulate,
11. Separately, co-sift cyclophosphamide, pregelatinized starch and croscarmellose.
12. Co sift talc and colloidal anhydrous silica-E and Ferric oxide yellow
13. Blend the granules of step 11, 12 and 13 in blender and lubricated with magnesium stearate to prepare the final composition of second layer Compression & Film Coating of Bilayer Tablet:
15. Bilayer tablets were compressed using blend of step 7 and blend of step 14 using rotary tablet compression machine.
16. Tablets were coated using coating solution containing polyethylene glycol 6000, polysorbate 80, sodiumcarboxymethyl cellulose, talc, titanium dioxide, eudragit NE30D, ferric oxide red, ferric oxide yellow and purified water.
17. Pack the film coated tablets in suitable pack using packaging machine.

Example 2B

Example 2B contains cyclophosphamide having D90 particle less than 100 microns with similar pharmaceutical composition and manufacturing process as example 2A.

Results for Content Uniformity of Example 2A and 2B

Example 2B (bilayer tablet comprises cyclophosphamide has D90 less than 100 microns) show better content uniformity and acceptance valve of 8.3 and meets the USP criteria as per revised <905> uniformity of dosage units.

Example 3: Bilayer Tablet

| Ingredients | Qty/Tab (mg)) |
|---|---|
| Capecitabine* | 700.00 |
| Microcrystalline Cellulose | 58.22 |
| Lactose anhydrous | 60.72 |
| Croscarmellose Sodium | 23.19 |
| HPMC E-5 | 32.46 |
| Purified Water | q.s. |
| Croscarmellose Sodium | 23.19 |
| Colloidal silicon dioxide | 4.64 |
| Magnesium Stearate | 18.55 |
| Total of Layer I | 930.00 |
| Microcrystalline cellulose | 93.83 |
| Dibasic calcium phosphate, dihydrate (milled) | 57.60 |
| Pregelatinized starch | 31.50 |
| Povidone K-90 | 5.10 |
| Purified water | q.s. |
| Cyclophosphamide # | 32.1 |
| Pregelatinized starch # | 6.90 |
| Croscarmellose Sodium | 15.00 |
| Talc | 5.10 |
| Colloidal anhydrous silica-E | 2.55 |
| Magnesium Stearate | 5.10 |
| Ferric oxide yellow | 0.23 |
| Total Layer II | 255.00 |
| Total Core Tablet weight | 1185.00 |
| Polyethylene glycol 4000 | 4.78 |
| Polysorbate 80 | 0.98 |
| Sodiumcarboxymethyl cellulose | 0.78 |
| Talc | 9.48 |
| Titanium Dioxide | 9.48 |
| Eudragit NE30D | 4.30 |
| | (14.350) |

| Ingredients | Qty/Tab (mg) |
|---|---|
| Ferric oxide yellow | 0.18 |
| Ferric oxide Red | 0.01 |
| Purified water | q.s. |
| Total coated tablet weight | 1215.00 |

Manufacturing Process:
Preparation of Capecitabine Layer:
1. Sift capecitabine, microcrystalline cellulose, lactose anhydrous and croscarmellose sodium, through ASTM 20# sieve.
2. Place materials of step 1 in fluid bed energizer and dry mix for 5 min at 50° C.
3. Dissolve hypromellose E5 in Purified Water using stirrer.
4. Granulate materials in fluid bed energizer using binder solution of step 3.
5. Dry the granules in fluid bed energizer at 55° C.
6. Pass the dried granules through ASTM 20# sieve.
7. Sift croscarmellose sodium through ASTM 20# and colloidal silicon dioxide through ASTM 40# sieve and mix with granules of step 6 in blender for 10 mins at 25 RPM.
8. Sift magnesium stearate through ASTM 40# sieve and mix with blend of step 7 for 3 mins.
Preparation of Cyclophosphamide Layer
9. Co sift Microcrystalline cellulose (Avicel PH 101), Dibasic calcium phosphate, dihydrate (milled), Pregelatinized starch (Starch 1500) and Povidone K-90 through 30#ASTM sieve.
10. Dry mix and granulate the blend of step 9 using Purified water. Dry the granules at 60° C. Mill the granules through co mill.
11. Separately, co-sift cyclophosphamide, pregelatinized starch (Starch 1500) and croscarmellose sodium through 40# ASTM sieve.
12. Co sift talc and colloidal anhydrous silica-E through 40#ASTM sieve. Ferric oxide yellow was sifted through 80# ASTM sieve.
13. Blend the granules of step 10, 11 and 12 in blender for 10 minutes.
14. Sift magnesium stearate through 40# sieve and mix with blend of step 1
Compression & Film Coating of Bilayer Tablet
15. Bilayer tablets were compressed using blend of step 8 and blend of step 14 using rotary tablet compression machine.
16. Tablets were coated using coating solution containing polyethylene glycol 6000, polysorbate 80, sodiumcarboxymethyl cellulose, talc, titanium dioxide, eudragit NE30D, ferric oxide red, ferric oxide yellow and purified water.
17. Pack the film coated tablets in suitable pack using packaging machine.

Example 4: Bilayer Tablet

| Ingredients | Qty./Tablet (mg) |
|---|---|
| Capecitabine* | 700.00 |
| Microcrystalline Cellulose | 58.70 |
| Lactose anhydrous | 73.45 |
| Croscarmellose Sodium | 23.38 |
| HPMC E-5 | 32.73 |
| Purified Water | q.s. |
| Croscarmellose Sodium | 23.38 |
| Colloidal silicon dioxide | 4.68 |
| Magnesium Stearate | 18.70 |
| Total of Layer I | 935.00 |
| Microcrystalline cellulose | 68.93 |
| Lactose monohydrate | 45.30 |
| Dibasic calcium phosphate, dihydrate | 39.30 |
| Pregelatinized starch | 31.50 |
| Povidone K-90 | 5.10 |
| Purified water | q.s. |
| Cyclophosphamide # | 30.0 |
| Pregelatinized starch # | 6.90 |
| Croscarmellose Sodium | 15.00 |
| Talc | 5.10 |
| Colloidal anhydrous silica-E | 2.55 |
| Magnesium Stearate | 5.10 |
| Ferric oxide yellow | 0.23 |
| Total Layer II | 255.00 |
| Total Core Tablet weight | 1190.00 |
| Opadry 20F520028 yellow | 42.00 |
| Purified water | q.s. |
| Total coated tablet weight | 1232.00 |

Manufacturing Process:
Preparation of Capecitabine Layer
1. Sift capecitabine, microcrystalline cellulose, lactose anhydrous and croscarmellose sodium, through ASTM 20# sieve.
2. Place materials of step 1 in fluid bed energizer and dry mix for 5 min at 50° C.
3. Dissolve hypromellose E5 in Purified Water using stirrer.
4. Granulate materials in fluid bed energizer using binder solution of step 3.
5. Dry the granules in fluid bed energizer at 55° C.
6. Pass the dried granules through ASTM 20# sieve.
7. Sift croscarmellose sodium through ASTM 20# and colloidal silicon dioxide through ASTM 40# sieve and mix with granules of step 6 in blender for 10 mins at 25 RPM.
8. Sift magnesium stearate through ASTM 40# sieve and mix with blend of step 7 for 3 mins.
Preparation of Cyclophosphamide Layer
9. Co sift microcrystalline cellulose, Dibasic calcium phosphate, dihydrate (milled), lactose monohydrate, pregelatinized starch (Starch 1500) and Povidone K-90 through 30#ASTM sieve.
10. Dry mix and granulate the blend of step 9 using Purified water. Dry the granules at 60° C. Mill the granules through co mill.
11. Separately, co-sift Cyclophosphamide, pregelatinized starch (Starch 1500) and croscarmellose sodium through 40# ASTM sieve.
12. Co sift talc and colloidal anhydrous silica-E through 40#ASTM sieve. Ferric oxide yellow was sifted through 80# ASTM sieve.
13. Blend the granules of step 10, 11 and 12 in blender for 15 minutes.
14. Sift magnesium stearate through 40# sieve and mix with blend of step 13 for 3 mins.

Compression & Film Coating of Bilayer Tablet
15. Bilayer tablets were compressed using blend of step 8 and blend of step 14 using rotary tablet compression machine.
16. Tablets were coated using opadry 20F520028 yellow containing hydroxypropyl methyl cellulose, hydroxypropyl cellulose, talc, polyethylene glycol, Iron oxide red & Iron oxide yellow.
17. Pack the film coated tablets in suitable pack using packaging machine.

Results:

|  | Cyclophosphamide | |
| --- | --- | --- |
|  | Example 3 $D90 < 100$ microns | Example 4 $D90 < 100$ microns |
| Content uniformity | 93.6%-104.2% | 93%-104.5% |
| Acceptance value | 8.3 | 8.9 |

We claim:

1. A pharmaceutical composition comprising cyclophosphamide and one or more pharmaceutically acceptable excipients, wherein cyclophosphamide has D90 particle size less than 100 microns.

2. The pharmaceutical composition according to claim 1, wherein the said pharmaceutical composition further comprises one or more pharmaceutical active ingredients.

3. The pharmaceutical composition according to claim 2, wherein the said pharmaceutical active ingredient is capecitabine or its pharmaceutically acceptable salts thereof.

4. The pharmaceutical composition according to claim 1, wherein the said pharmaceutical composition is present in a solid oral dosage form comprising of monolayer tablet, bilayer tablet, multilayer tablet, film-coated tablet, powders, lozenges, sachets and hard gelatin capsules.

5. The pharmaceutical composition according to claim 4, wherein the said pharmaceutical composition is in the form of bilayer tablet.

6. The pharmaceutical composition according to claim 5, wherein the bilayer tablet comprises a first layer & second layer, wherein the first layer comprises capecitabine and one or more excipients, and the second layer comprises cyclophosphamide and one or more excipients.

7. The pharmaceutical composition according to claim 5, wherein the first layer comprises capecitabine in the amount of 10 to 1500 mg and one or more excipients, and the second layer comprises cyclophosphamide in the amount of 20 to 80 mg and one or more excipients.

8. The pharmaceutical composition according to claim 1, wherein the said pharmaceutical composition have a content uniformity between 95% and 105% and acceptance value less than 15 as per USP <905> uniformity of dosage units.

9. A pharmaceutical composition comprising cyclophosphamide and capecitabine in the form of bilayer tablet, wherein the first layer comprises capecitabine and one or more excipients, and the second layer comprises cyclophosphamide and one or more excipients, wherein the cyclophosphamide has D90 particle size less than 100 microns.

10. A pharmaceutical composition comprising cyclophosphamide and capecitabine in the form bilayer tablet, wherein the first layer comprises capecitabine and one or more excipients, and the second layer comprises cyclophosphamide and one or more excipients, wherein the cyclophosphamide has D90 particle size less than 100 microns; wherein the said pharmaceutical composition have a content uniformity between 95% and 105% and acceptance value less than 15 as per USP <905> uniformity of dosage units.

* * * * *